US008788012B2

(12) United States Patent
Ubelhart et al.

(10) Patent No.: US 8,788,012 B2
(45) Date of Patent: Jul. 22, 2014

(54) METHODS AND APPARATUS FOR AUTOMATICALLY REGISTERING LESIONS BETWEEN EXAMINATIONS

(75) Inventors: Istvan Ubelhart, Budapest (HU); Balazs Cziria, Vorosmarty (HU)

(73) Assignee: General Electric Company, Schenectady, NY (US)

(*) Notice: Subject to any disclaimer, the term of this patent is extended or adjusted under 35 U.S.C. 154(b) by 1346 days.

(21) Appl. No.: 11/603,701

(22) Filed: Nov. 21, 2006

(65) Prior Publication Data

US 2008/0118132 A1 May 22, 2008

(51) Int. Cl.
| A61B 5/05 | (2006.01) |
| G06K 9/00 | (2006.01) |
| A61B 6/00 | (2006.01) |
| A61B 5/11 | (2006.01) |

(52) U.S. Cl.
CPC ............ *A61B 6/5235* (2013.01); *A61B 5/1113* (2013.01)
USPC .......................................... 600/407; 382/131

(58) Field of Classification Search
USPC ........................................................ 600/407
See application file for complete search history.

(56) References Cited

U.S. PATENT DOCUMENTS

| 6,597,762 | B1 * | 7/2003 | Ferrant et al. .................... 378/62 |
| 7,615,008 | B2 * | 11/2009 | Zhang et al. .................. 600/437 |
| 2004/0030246 | A1 * | 2/2004 | Townsend et al. ............ 600/427 |
| 2005/0047544 | A1 * | 3/2005 | Fu et al. ............................ 378/63 |
| 2005/0182295 | A1 * | 8/2005 | Soper et al. .................... 600/117 |
| 2005/0267348 | A1 * | 12/2005 | Wollenweber et al. ....... 600/407 |
| 2006/0002601 | A1 * | 1/2006 | Fu et al. ......................... 382/132 |
| 2006/0002632 | A1 * | 1/2006 | Fu et al. ......................... 382/294 |
| 2006/0030768 | A1 * | 2/2006 | Ramamurthy et al. ....... 600/407 |
| 2006/0050943 | A1 * | 3/2006 | Ozaki et al. ................... 382/131 |
| 2006/0104494 | A1 * | 5/2006 | Collins et al. ................. 382/128 |
| 2007/0160312 | A1 * | 7/2007 | Blaffert et al. ................ 382/294 |
| 2007/0167697 | A1 * | 7/2007 | Avila et al. .................... 600/407 |

OTHER PUBLICATIONS

Cardiac MRI Anatomical Atlas, Discussion of MRI & Links to other sites, http://www.scmr.org/education/atlas/intro/mrilinks.htm.
Anatomical terms of location, http://en.wikipedia.org/wiki/Sagitally.
Anatomy of the brain, Wayne State University, http://www.med.wayne.edu/diagRadiology/Anatomy_Modules/brain/brain.html.
Computed tomography, http://en.wikipedia.org/wiki/Computed_axial_tomography.

* cited by examiner

*Primary Examiner* — Tse Chen
*Assistant Examiner* — Hien Nguyen
(74) *Attorney, Agent, or Firm* — The Small Patent Law Group; Dean D. Small

(57) ABSTRACT

Methods and apparatus for automatically registering lesions between examinations are provided. The methods include performing a rigid registration using computed tomography (CT) images from a first image set and a second image set and performing a local non-rigid registration using positron emission tomography (PET) images from the first image set and the second image set. The methods further include automatically locating lesions on the second image set from the first image set.

11 Claims, 6 Drawing Sheets

METHODS AND APPARATUS FOR AUTOMATICALLY REGISTERING LESIONS BETWEEN EXAMINATIONS

BACKGROUND OF THE INVENTION

This invention relates generally to medical imaging systems and, more particularly, to automatically matching lesions in medical images acquired by a medical imaging system at different times.

Positron emission tomography (PET) generally involves acquiring images showing physiologic data based on the detection of radiation from the emission of photons. Images acquired using PET may be used to evaluate different conditions and diseases, for example, to detect cancer and evaluate the progression or regression of the cancer. Other examinations using PET include, for example, heart scans or brain scans.

PET scans are increasingly being used in connection with other types of medical scans, including, for example, with computed tomography (CT) scans and/or magnetic resonance imaging (MRI) scans. The combination of the images from the scans, often referred to as co-registration, provides both anatomic and metabolic information on a single image. Combination or multimodality scanners are also available to perform both scans during the same scanning session.

However, registration is an issue when performing a first examination, such as a baseline examination, and a subsequent examination at a later time. For example, reading PET examinations and examining tumor response between a baseline image and a follow-up image is a very time consuming process that often results in reduced patient examination throughput. In particular, when evaluating the baseline image and comparing to the follow-up image, one of the slow and tedious steps is finding the lesions on the follow-up image previously identified on the baseline image and matching corresponding lesions from the two images. This process not only adds time and cost to overall examination, but can result in errors and potential improper diagnosis of the lesions that are not properly identified and matched in the images.

BRIEF DESCRIPTION OF THE INVENTION

In one embodiment, a method for lesion matching in medical images is provided. The method includes performing a rigid registration using computed tomography (CT) images from a first image set and a second image set and performing a local non-rigid registration using positron emission tomography (PET) images from the first image set and the second image set. The method further includes automatically locating lesions on the second image set from the first image set.

In another embodiment, a medical imaging apparatus having a first modality unit and a second modality unit, an image processor, a display, and a memory is provided. The medical imaging apparatus is controlled by a computer configured to operate the medical imaging apparatus to produce computed tomography (CT) images and positron emission tomography (PET) images using the first and second modality units, the image processor, the display, and the memory. The memory has stored therein instructions configured to instruct the computer to generate an image having identified lesions displayed thereon. The instructions comprise instructions configured to instruct the computer to perform a rigid registration using CT images from a first image set and a second image set, perform a local non-rigid registration using PET images from the first image set and the second image set, and automatically locating lesions on the second image set from the first image set.

In yet another embodiment, a machine-readable medium or media having instructions recorded thereon configured to instruct a computer to generate an image having identified lesions displayed thereon is provided. The instructions comprise instructions configured to instruct the computer to perform a rigid registration using computed tomography (CT) images from a first image set and a second image set, perform a local non-rigid registration using positron emission tomography (PET) images from the first image set and the second image set, and automatically locate lesions on the second image set from the first image set.

DETAILED DESCRIPTION OF THE INVENTION

Figure 1:
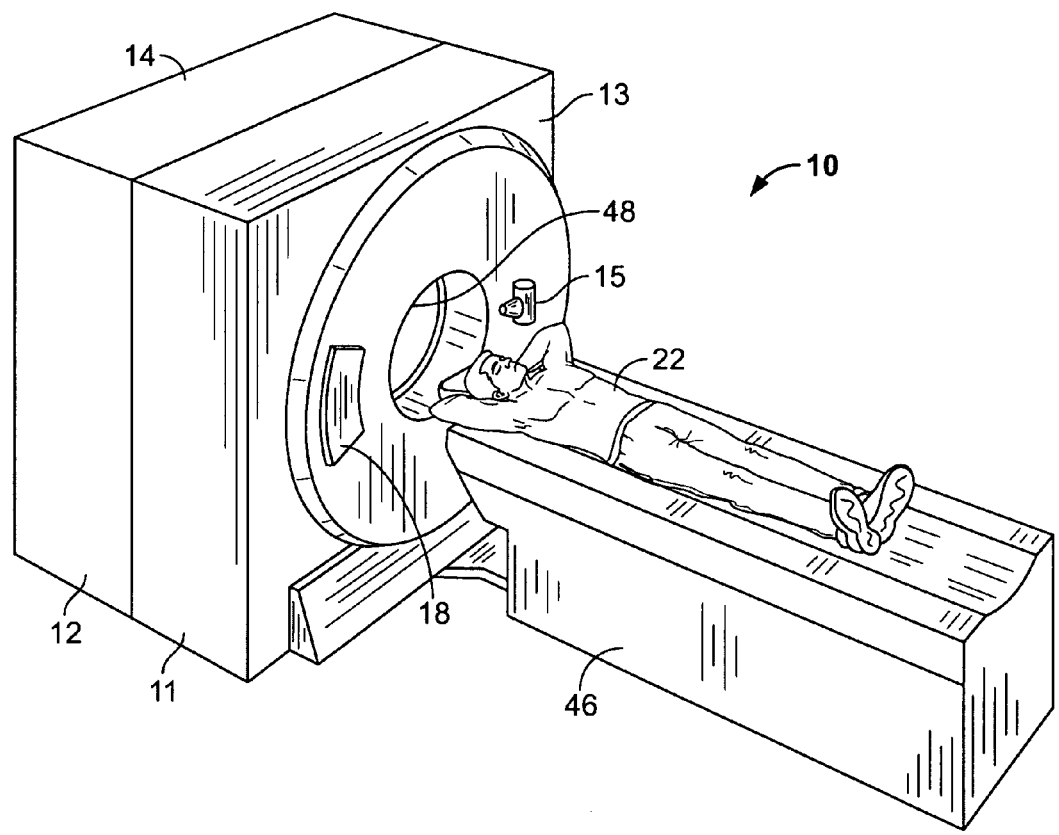
FIG. 1 is a perspective view of an exemplary imaging system.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments of the present invention in which data representing an image is generated but a viewable image is not. However, many embodiments generate (or are configured to generate) at least one viewable image.

Embodiments of the present invention provide a method of registering different positron emission tomography (PET) images and computed tomography (CT) images acquired at different times to match corresponding lesions. Technical effects of the present invention include, but are not limited to processing image data from different PET/CT images to match lesions and that is useful in detecting a change in the lesions from a first examination to a subsequent follow-up examination. It should be noted that as used herein, unless referring to an image actually being displayed, the scope of the subject matter referred to by the term "image" is also intended to include data representing an image, for example, an image in a form useful for processing by a computer.

Figure 2:
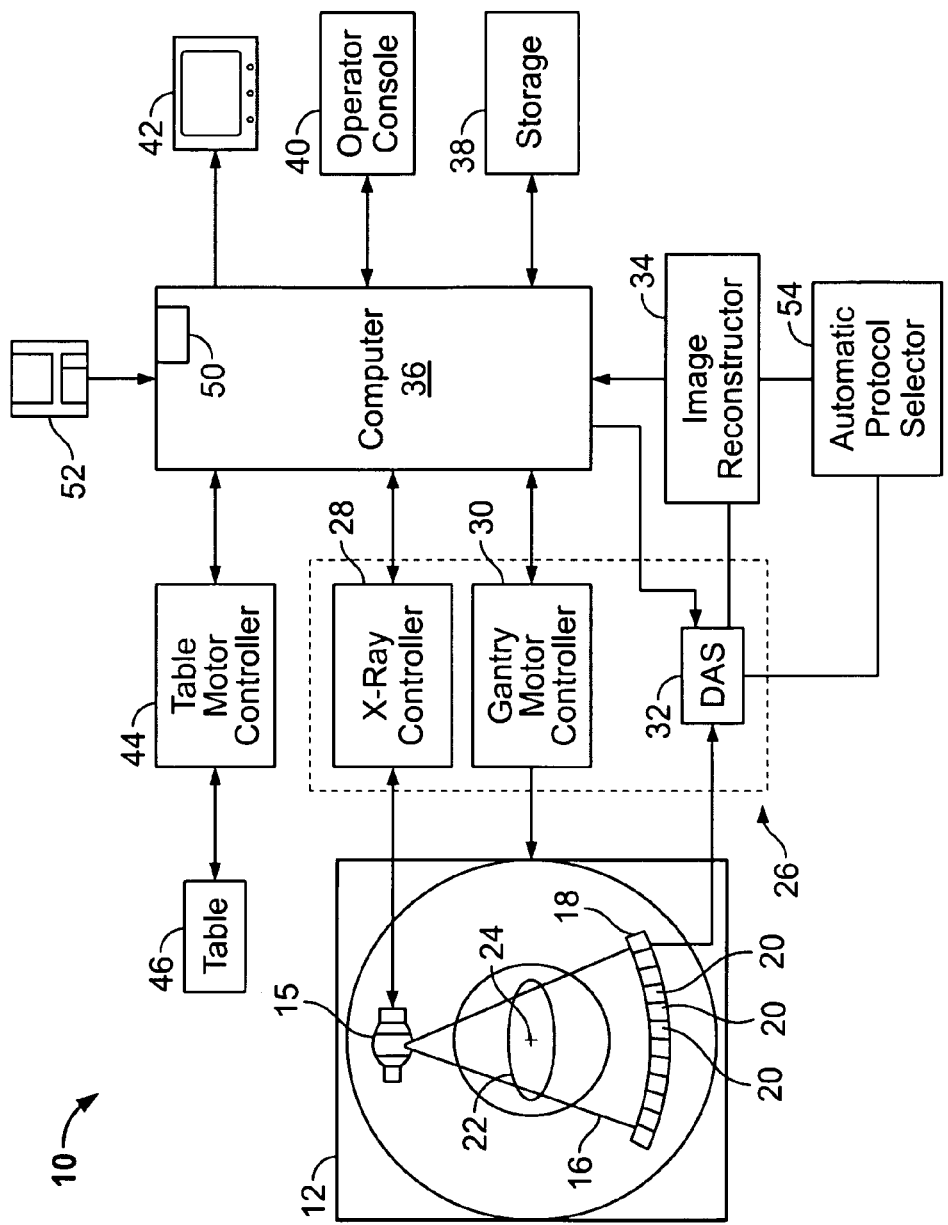
FIG. 2 is a schematic block diagram of the imaging system shown in FIG. 1.

FIG. 1 is a perspective view of an exemplary imaging system 10 constructed in accordance with various embodiments of the invention. FIG. 2 is a schematic block diagram of the imaging system 10 (shown in FIG. 1). In the exemplary embodiment, the imaging system 10 is a multi-modal imaging system and includes a first modality unit 11 and a second modality unit 12. The modality units 11 and 12 enable the system 10 to scan an object, for example, a patient, in a first modality using the first modality unit 11 and to scan the object in a second modality using the second modality unit 12. The system 10 allows for multiple scans in different modalities to facilitate an increased diagnostic capability over single modality systems. In one embodiment, the multi-modal imaging system 10 is a Computed Tomography/Positron Emission Tomography (CT/PET) imaging system 10. The CT/PET system 10 includes a first gantry 13 associated with the first modality unit 11 and a second gantry 14 associated with the second modality unit 12. In alternative embodiments, modalities other than CT and PET may be employed with the imaging system 10. The gantry 13, in an embodiment, includes the first modality unit 11 that has an x-ray source 15 that projects a beam of x-rays 16 toward a detector array 18 on the opposite side of the gantry 13. The detector array 18 is formed by a plurality of detector rows (not shown) including a plurality of detector elements 20 that together sense the projected x-rays that pass through an object, such as a patient 22. Each detector element 20 produces an electrical signal that represents the intensity of an impinging x-ray beam and allows estimation of the attenuation of the beam as the beam passes through the object or patient 22.

In other embodiments, the system 10 includes only a single gantry having a first rotor configured to carry the first modality system and a second rotor configured to carry the second modality system. In various other embodiments the system 10 includes only one modality, such as CT or PET.

During a scan to acquire x-ray projection data the gantry 13 and the components mounted thereon rotate about an examination axis 24. FIG. 2 shows only a single row of detector elements 20 (i.e., a detector row). However, the detector array 18 may be configured as a multislice detector array having a plurality of parallel detector rows of detector elements 20 such that projection data corresponding to a plurality of slices can be acquired simultaneously during a scan. To acquire emission data, for example, during a PET scan, the gantry 14 rotates one or more gamma cameras (not shown) about the examination axis 24. The gantry 14 may be configured for continuous rotation during an imaging scan and/or for intermittent rotation between imaging frames.

The rotation of the gantries 13 and 14, and the operation of the x-ray source 15 are controlled by a control mechanism 26 of the system 10 (e.g., CT/PET system). The control mechanism 26 includes an x-ray controller 28 that provides power and timing signals to the x-ray source 15 and a gantry motor controller 30 that controls the rotational speed and position of the gantry 13 and the gantry 14. A data acquisition system (DAS) 32 of the control mechanism 26 samples data from the detector elements 20 and the gamma cameras and conditions the data for subsequent processing. An image reconstructor 34 receives sampled and digitized x-ray data and emission data from the DAS 32 and performs high-speed image reconstruction. The reconstructed image is transmitted as an input to a computer 36 that stores the image in a storage device 38.

The computer 36 also receives commands and scanning parameters from an operator via console 40 that has an input device, such as, a keyboard. An associated display 42 allows the operator to observe the reconstructed image and other data from the computer 36. Operator supplied commands and parameters are used by the computer 36 to provide control signals and information to the DAS 32, the x-ray controller 28 and the gantry motor controller 30. In addition, the computer 36 operates a table motor controller 44 that controls a motorized table 46 to position the patient 22 in the gantry 13 and 14. Specifically, the table 46 moves portions of the patient 22 through the gantry opening 48.

In one embodiment, the computer 36 includes a read/write device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, the computer 36 executes instructions stored in firmware (not shown). The computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. The system 10 may also includes a plurality of other detectors, for example, PET detectors (not shown) including a plurality of detector elements. The PET detectors and the detector array 18 both detect radiation and are both referred to herein as radiation detectors.

An automatic protocol selector 54 is communicatively coupled to the DAS 32 and the image reconstructor 34 to transmit settings and parameters for use by the DAS 32 and the image reconstructor 34 during a scan and/or image reconstruction and image review. Although the automatic protocol selector 54 is illustrated as a separate component, it should be understood that functions performed by the automatic protocol selector 54 may be incorporated into functions performed by, for example the computer 36. Accordingly, the automatic protocol selector 54 may be embodied in a software code segment executing on a multifunctional processor or may embodied in a combination of hardware and software.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station, non-destructive testing systems, etc.

In operation, before an examination begins, a radioactive substance is produced, for example, in a machine called a cyclotron and attached, or tagged, to a natural body compound, most often glucose, but sometimes water or ammonia. Once this substance is administered to the patient (e.g., by intravenous injection), the radioactivity localizes in the appropriate areas of the body and is detected by the rotating PET scanner. Different colors or degrees of brightness on a PET image generally represent different levels of tissue or organ function. For example, because healthy tissue uses glucose for energy, this healthy tissue accumulates some of the tagged glucose, which will show up on the PET images. However, cancerous tissue, which uses more glucose than normal tissue, will accumulate more of the substance and appear brighter than normal tissue on the PET images. A CT scan may be performed immediately before, immediately after and/or simultaneously with the PET scan. Thus, at the end of a single scanning session with the imaging system 10, both CT image data, for example, anatomic data, and PET image data, for example, metabolic data are acquired.

Figure 3:
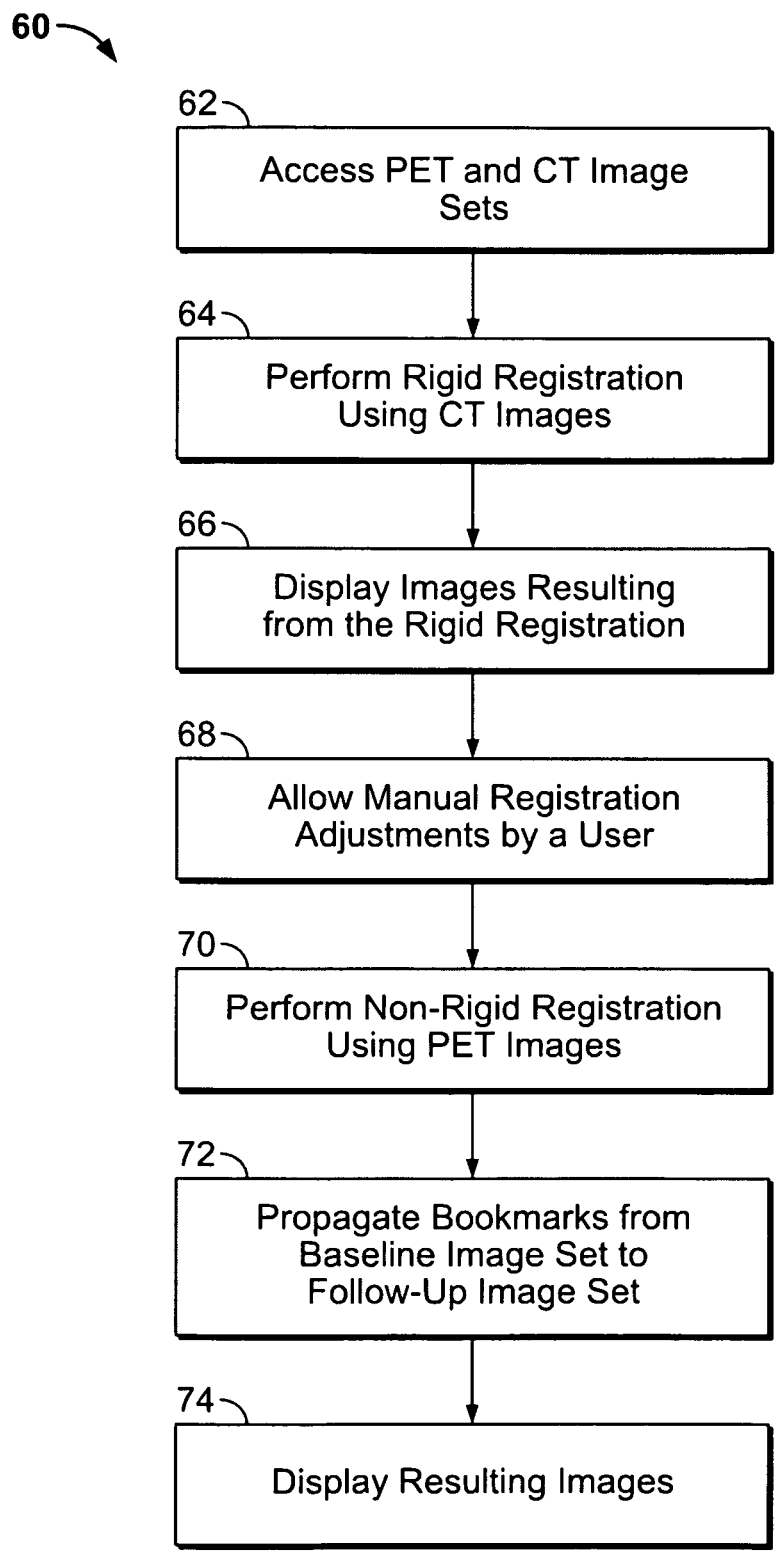
FIG. 3 is a flowchart of a method for registering images to automatically match lesions between a first image or set of images and a second image or set of images in accordance with various embodiments of the invention.

Various embodiments provide a method 60 as shown in FIG. 3 for registering images to automatically match lesions between a first image or set of images (baseline images) and a second image or set of images (follow-up images) acquired at different times. For example, the first images may be acquired at a first examination and a month later the follow-up images acquired during a follow-up examination. In one embodiment, PET images are registered to automatically match lesions.

It should be noted that in various embodiments corresponding CT images are acquired as the same time as the PET images are acquired. More particularly, a complete scanning process includes acquiring both PET images and CT images of a patient, for example, a region of interest of the patient.

Specifically, the method 60 includes accessing acquired PET and CT image sets at 62. For example, a first PET and CT image set (referred to herein as PET1 and CT1) acquired, for example, during a baseline examination, are accessed. Further, a second PET and CT image set (referred to herein as PET2 and CT2) acquired, for example, during a follow-up examination are accessed. The images generally include PET image data and CT image data that include information of interest. For example, the image data may include images or regions of interest that include, for example, lesions or other conditions that may be bookmarked. It should be noted that the first and second PET image sets and the first and second CT image sets may be acquired using a combined PET/CT machine (e.g., scanner or imaging system), thereby providing hardware based multi-modality registration of the first and second image sets.

Thereafter, at 64 an automatic rigid registration between the image sets is performed using the CT1 images and the CT2 images. The rigid registration is essentially a full body registration of the entire data sets defining the CT1 images and the CT2 images. During this rigid registration the image data may be transformed in the three-dimensional (3D) space to align the image sets. For example, the CT1 images may be slighted tilted with respect to the CT2 images. Accordingly, either the CT1 images or the CT2 images are tilted to align both data sets. This process is performed using any known rigid registration process, for example, mutual information based registration with only the rigid parameters being modified (e.g., the rotation, scaling and translation parameters). The rigid registration process may include selecting anatomical or other features/points/landmarks and the images aligned using theses feature or points along with detected edges or borders within the images. Alternatively, different markers may be used to identify known anatomical locations. Different shaped templates also may used and compared in the different image sets in order to provide the rigid registration. The rigid registration also may be based on curved contours, for example, of bones within the image. The registration may be volume based or surface based. However, it should be appreciated that any rigid registration process may be performed that includes optimizing or calculating a certain comparable criteria or similarity measure. The process is essentially a linear registration of the CT1 images and the CT2 images that transforms the different data sets that may not be entirely aligned into one coordinate system that includes aligned images. The linear transformation may use a combination of translation, rotation, global scaling, shear and perspective components, among others.

Image registration algorithms for performing the rigid registration may generally include area based methods and feature based methods. In area based image registration methods, the algorithm analyzing the structure of the image use, for example, correlation metrics, Fourier properties and other means of structural analysis. Accordingly, the overall structure of the images is analyzed. In feature based registration methods, mapping is generally performed to correlate image features such as lines, curves, points, line intersections, boundaries, etc.

Image similarity-based methods are used in various embodiments and include a transformation model that is applied to reference image coordinates to locate corresponding coordinates in the target image space (e.g., from CT1 images to CT2 images), an image similarity metric that quantifies the degree of correspondence between features in both image spaces achieved by a given transformation, and an optimization algorithm that attempts to maximize image similarity by changing the transformation parameters. The choice of an image similarity measure may depend on the nature of the images to be registered. Some image similarity measures that may be used include, for example, cross-correlation, mutual information, mean-square difference and ratio image uniformity.

Figure 4:
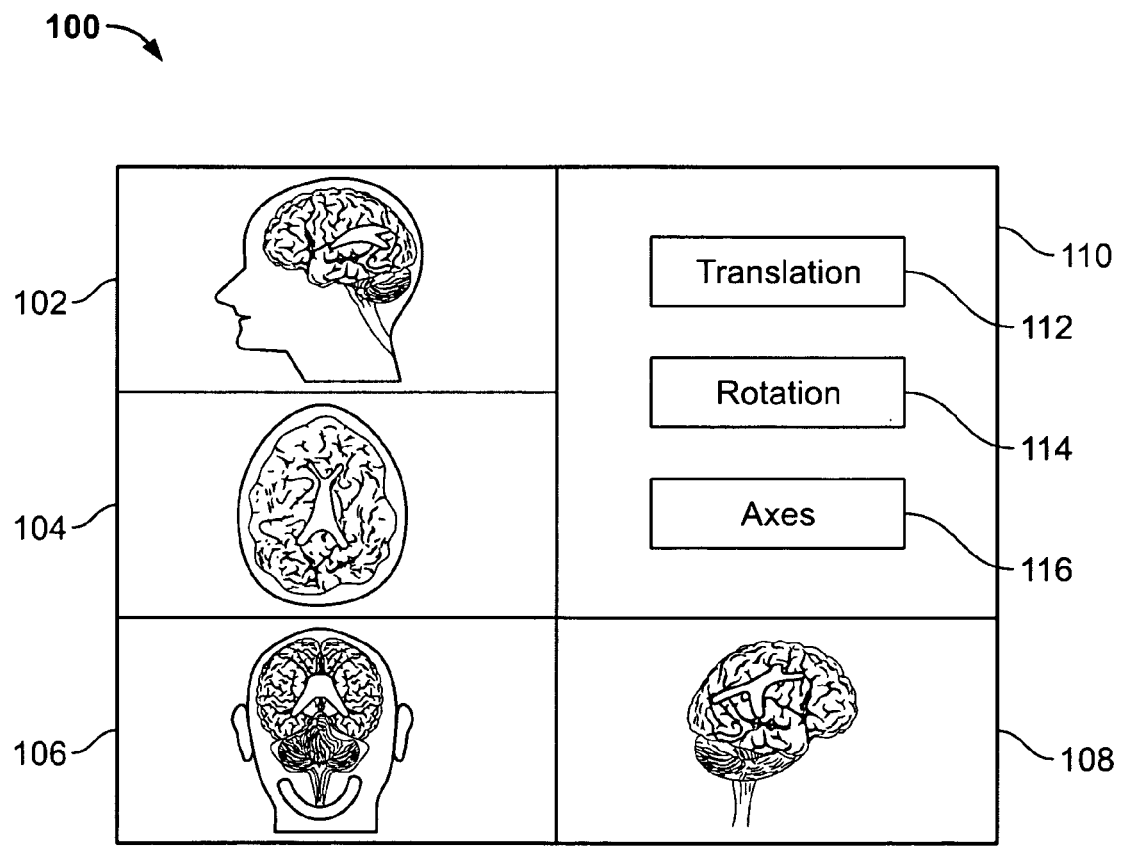
FIG. 4 is a display illustrating different image views formed in accordance with various embodiments of the invention.
Figure 5:
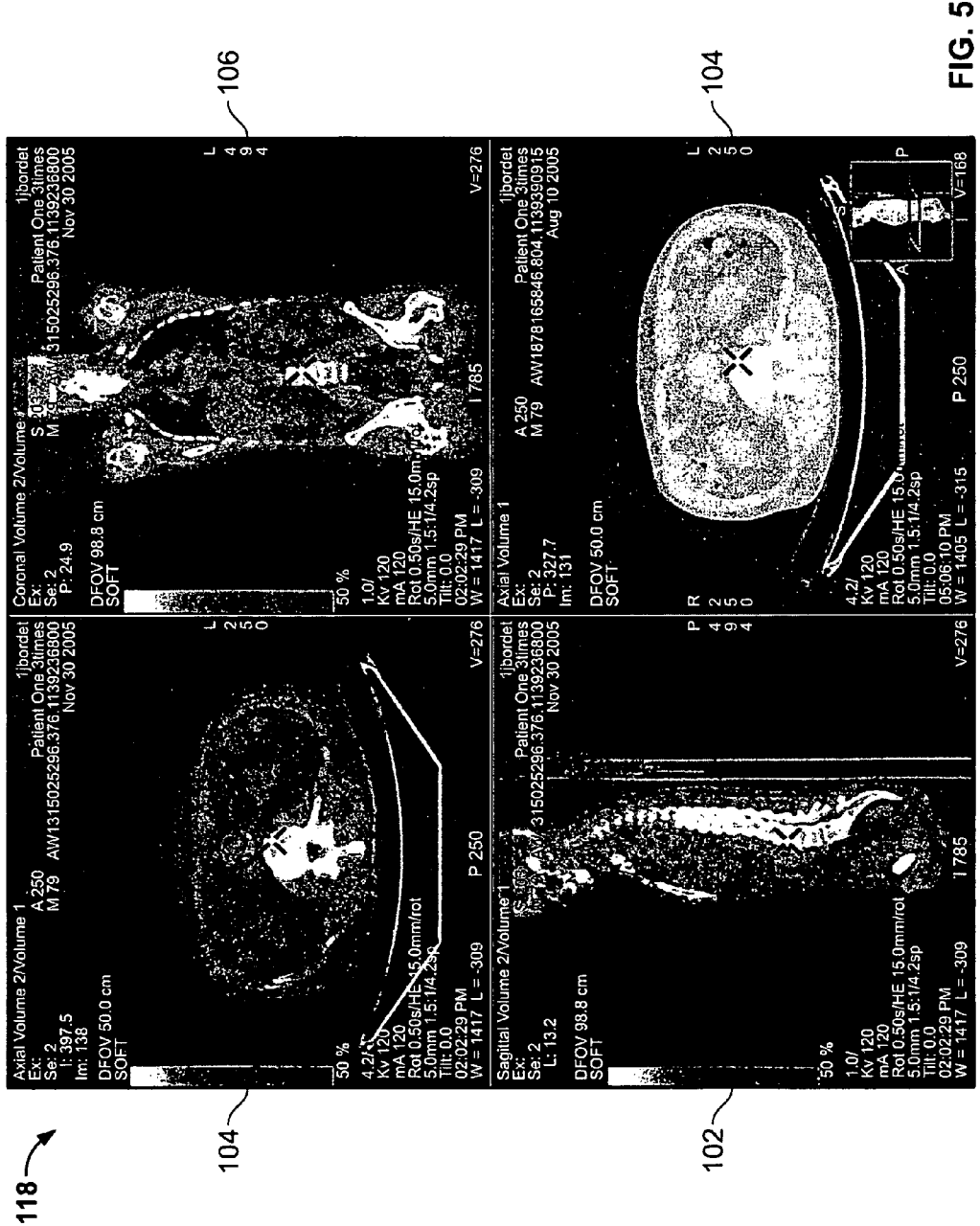
FIG. 5 is a display illustrating different image views of fused views formed in accordance with various embodiments of the invention.

Once the rigid registration is performed using the CT1 images and CT2 images at 64, the results of the rigid registration are displayed at 66. More particularly, and as shown in FIG. 4, a display 100 may be provided showing different views of the images. For example, a sagittal image view 102, an axial image view 104 and a coronal image view 106 may be displayed in a mutli-image format. The illustrated example shows multiple views of a head scan, however, the image may be of any regions of interest, for example, the heart, lungs, etc. Additionally, a 3D volume rendered image view 108 also may be provided. An example of registered CT images in fused views is illustrated in the display 118 shown in FIG. 5.

It should be noted that the images may be formed using any image reconstruction technique, for example, using a soft kernel, a bone kernel, a standard kernel, etc. and a cone beam reconstruction or a fan beam reconstruction algorithm.

Referring again to FIG. 3, manual adjustments to the rigid registered images may be provided at 68. For example, the display 100 shown in FIG. 4 may include a user interface portion 110 configured to receive user inputs that allow for the manual adjustment of the registration of the image views displayed. The user may select one of the views and change the translation of an image view using a translation selection member 112, change the rotation of an image view using a rotation selection member 114 and change the axes of an image view using an axes selection member 116. Other options may be provided as desired or needed, for example, a selection member that allow changing of scaling. The activation of any of the selection members 112, 114 or 116 may provide additional selectable options for that particular operation, such as, in a drop down menu. A user may provide inputs using, for example, the operator console 40 of the imaging system 10 (both shown in FIG. 2). Thus, a user may define a translation and/or rotation around arbitrary axes between the two examinations including the two image sets.

Referring again to FIG. 3, after manual adjustments are provided, if any, a local non-rigid registration is automatically performed at 70 using the PET images, and in particular, the PET1 images and the PET2 images. In particular, certain regions, such as, lesions in the image sets that are bookmarked in the baseline images (hereafter baseline bookmarks), namely the CT1 images and the PET1 images, which may be a fused image, define a region for the local non-rigid registration. Specifically, the region is defined by an area including the baseline bookmarks. This area is typically smaller than the overall area included in the image data sets and generally defines one or more regions of interest. For example, the area encompassing the lesions is typically smaller than the entire data set included in the full body rigid registration. It should be noted that when reference is made herein to full body this does not necessarily refer to the entire patient body, but to the full data set for the acquired images.

The local registration is a non-rigid or elastic registration that includes non-rigid transformations. These non-rigid transformations allow local warping of image features and provide registrations that account for local deformations. Non-rigid transformation approaches include, for example, polynomial warping, interpolation of smooth basis functions (thin-plate splines and wavelets), and physical continuum models (viscous fluid models and large deformation diffeomorphisms). The local non-rigid registration is performed using the PET images, and in particular, the PET1 images and the PET2 images. The local non-rigid registration may include, for example, warping of points or landmarks and providing a best fit along a contour with interpolation and correlation of the points or landmarks. Alternatively, a blending process may be performed that compares image voxels and blends corresponding regions. In general, the local non-rigid registration includes any type of elastic deformation model that allows for variations or movements in the different image sets.

Once the local non-rigid registration is performed using the PET1 images and the PET2 images, bookmarks are propagated from the baseline image set to the follow-up image set at 72. The bookmarks may define the coordinate for a particular lesion or other region of interest. In particular, the bookmarks are propagated from the PET1 images to the PET2 images. It should be noted that the CT images also define an anatomic mapping between the PET images. Additionally, a local matching also may be performed on the follow-up PET images, namely, the PET2 images, in the proximity of the point determined by the local non-rigid registration computed using the CT data. This local matching can be performed using the non-rigid parameters or local rigid registration with optimization using similarity measures (e.g., maximizing the mutual information, maximum covariance match, etc.). This local matching further increases the probability of accurately determining the location of the follow-up lesion, for example, if the lesion has shifted between the first and second examinations. Accordingly, the bookmark in the PET1 image automatically points to the bookmark in the PET2 image. Known bookmarks are thus automatically moved from one image to another image (usually a later in time image). It should be noted that when the localized registration is performed using the PET images a corresponding mapping is provided in the CT images and vice versa.

Figure 6:
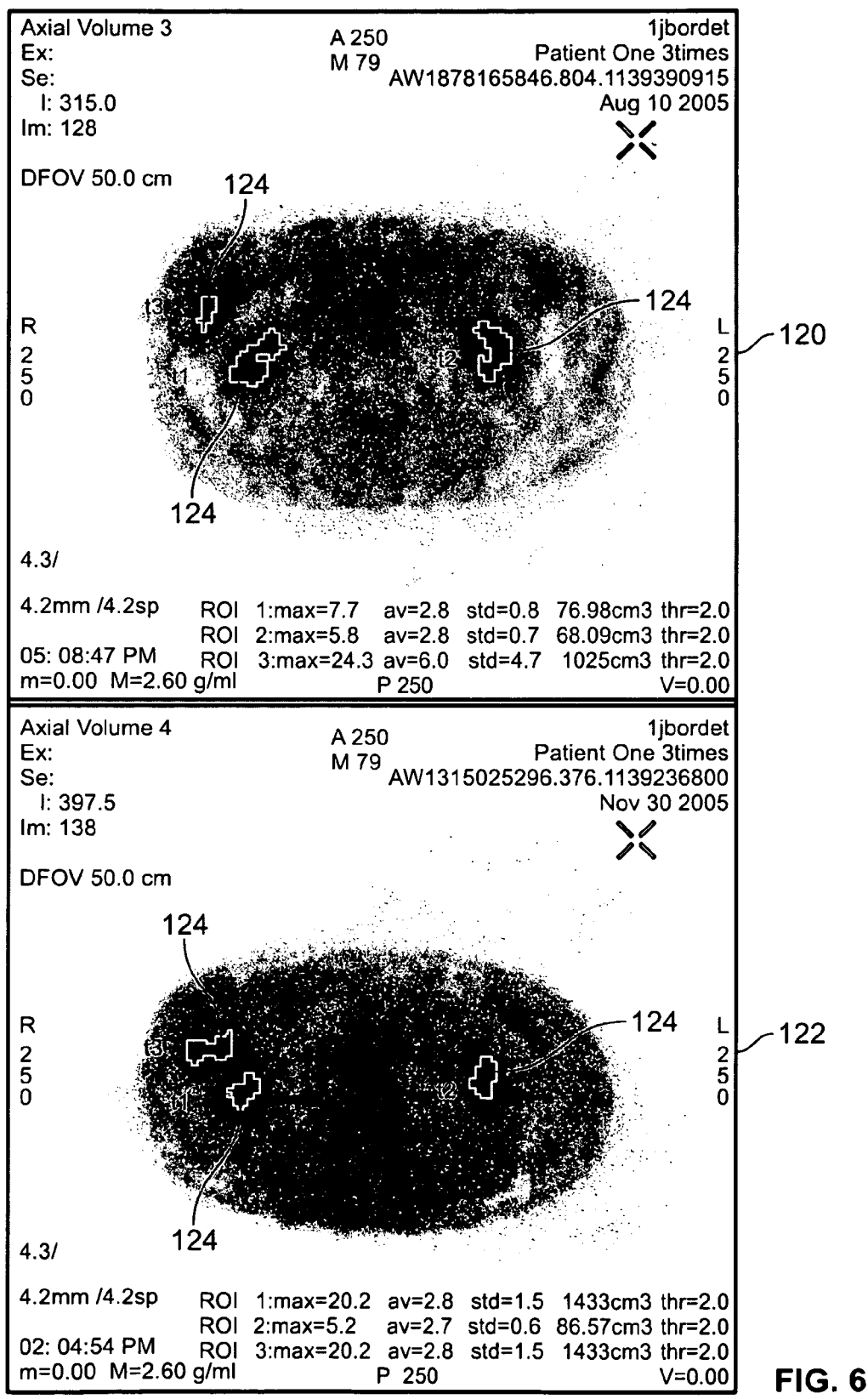
FIG. 6 is a display illustrating a baseline image and a follow-up image showing matched lesions in accordance with various embodiments of the invention.

Finally, the resulting images 120 and 122 are displayed at 74 as shown in FIG. 6. This again may include displaying different views of the images and providing the images in different formats. The original and follow-up images also may be displayed simultaneously for comparison. As shown, bookmarked regions 124 (e.g., visual marks) identifying segmented lesions are automatically located from the baseline image 120 to the follow-up image 122. It should be noted that the bookmark IDs indicate the mapping.

Thus, the various embodiments of the invention limit the search space for registration and the information used, namely the location of baseline bookmarks, which is always available during the workflow as an already acquired examination is compared to a new examination. No user intervention is needed to determine the area of interest. Further, both anatomical and functional information is used in a combined manner to provide the image registration for matching, for example, matching lesions between examinations.

It should be noted that the various embodiments may be applied to different imaging modalities, such as MRI, SPECT, etc. Also, the different registration processes may be performed on different image types, for example, the local non-rigid registration may be performed using CT images.

While the invention has been described in terms of various specific embodiments, those skilled in the art will recognize that the various embodiments of the invention can be practiced with modification within the spirit and scope of the claims.

What is claimed is:

1. A method for lesion matching in medical images, said method comprising:
    obtaining a first set of computed tomography (CT) images fused to a first set of positron emission tomography (PET) images at a first point in time that form a baseline fused data set;
    obtaining a second set of CT images fused to a second set of PET images at a different second point in time to form a follow-up fused data set;
    performing a rigid registration between the first set of CT images and the second set of CT images to define an anatomical mapping between the baseline and follow-up fused data sets;
    identifying a baseline bookmarked region of the first set of PET images using a plurality of bookmarks;
    performing a local non-rigid registration between the baseline bookmarked region, that is encompassed by the plurality of bookmarks, and a corresponding region in the second set of PET images;
    automatically propagating the bookmarks in the first set of PET images to the second set of PET images utilizing the local non-rigid registration, the anatomical mapping defined by the rigid registration between the baseline and follow-up fused data sets; and
    displaying the bookmarks in the corresponding region in the second set of PET images to automatically match lesions on at least one PET image in the second set of PET images.

2. A method in accordance with claim 1 wherein the first and second sets of CT images and the first and second sets of PET images are acquired using a combined PET/CT machine providing hardware based multi-modality registration of the baseline and follow-up fused data sets.

3. A method in accordance with claim 1 wherein the baseline fused data set comprises baseline images and the follow-up fused data set comprises follow-up images acquired at a time subsequent to the baseline fused data set.

4. A method in accordance with claim 1 further comprising displaying a plurality of views of images resulting from the rigid registration.

5. A method in accordance with claim 4 further comprising allowing manual user adjustment of the rigid registration.

6. A method in accordance with claim 5 wherein the user adjustment comprises one of translation, scaling and rotation adjustment.

7. A method in accordance with claim 1 wherein the local non-rigid registration is based on the location of a plurality of bookmarks identifying the lesions.

8. A method in accordance with claim 1 wherein the rigid registration comprises a linear registration.

9. A method in accordance with claim 1 wherein the local non-rigid registration comprises a non-linear registration.

10. A method in accordance with claim 1 wherein the baseline and follow-up fused data sets are each acquired using a single imaging system.

11. A method in accordance with claim 1 further comprising:
   identifying a lesion in the first set of PET images using the plurality of bookmarks; and
   propagating the plurality of bookmarks from the first set of PET images to the second set of PET images to automatically locate the lesion on the second set of PET images.

\* \* \* \* \*